United States Patent
Seip

(10) Patent No.: US 6,642,047 B2
(45) Date of Patent: Nov. 4, 2003

(54) EXOTHERMIC CHEMISTRY AND METHOD FOR GENERATING AN ANAEROBIC ENVIRONMENT

(75) Inventor: William Francis Seip, Baltimore, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 244 days.

(21) Appl. No.: 09/895,953

(22) Filed: Jun. 29, 2001

(65) Prior Publication Data

US 2003/0092173 A1 May 15, 2003

(51) Int. Cl.[7] ............................................... C12M 1/00
(52) U.S. Cl. ................................ 435/303.2; 435/307.1; 435/801; 252/186.1; 252/188.1; 252/188.25; 252/188.28
(58) Field of Search ....................... 435/303.2, 801, 435/307.1; 252/186.1, 188.1, 188.25, 188.28

(56) References Cited

U.S. PATENT DOCUMENTS

| | | | | |
|---|---|---|---|---|
| 4,377,554 A | * | 3/1983 | Johnson | 422/239 |
| 4,562,051 A | * | 12/1985 | Stoermer et al. | 423/219 |
| 4,976,931 A | * | 12/1990 | Stoermer et al. | 422/211 |
| 5,046,479 A | * | 9/1991 | Usui | 126/204 |
| 5,057,285 A | * | 10/1991 | Belt et al. | 422/236 |
| 5,236,617 A | * | 8/1993 | Ueno et al. | 252/188.28 |

* cited by examiner

Primary Examiner—David A. Redding
(74) Attorney, Agent, or Firm—Bruce S. Weintraub

(57) ABSTRACT

The present invention provides a method and device for creating an environment in a container that is suitable for growing anaerobic bacteria. The device utilizes exothermic chemistry to deplete oxygen and drive the decomposition of a bicarbonate present in the closed system. The decomposition of the bicarbonate results in the release of carbon dioxide. The result of this exothermic reaction and decomposition of the bicarbonate in the closed system results in a suitable oxygen depleted, carbon dioxide enriched atmospheric environment for the growth of anaerobic bacteria. The device is formed of an air permeable package containing a heat generating composition and a bicarbonate. The air-permeable package is contained within an outer wrap that forms an air barrier to the air-permeable package. To activate the heat generating composition, the outer wrap is removed to expose the air-permeable package to the oxygen within the container.

5 Claims, No Drawings

EXOTHERMIC CHEMISTRY AND METHOD FOR GENERATING AN ANAEROBIC ENVIRONMENT

BACKGROUND OF THE INVENTION

Field of the Invention

The present invention relates generally to producing an anaerobic environment. In particular, the present invention relates to a device that utilizes exothermic chemistry to deplete oxygen and generate carbon dioxide to create an environment for the growth of anaerobic microorganisms. The present invention also relates to a method for generating such an anaerobic environment.

DISCUSSION OF THE BACKGROUND

In general, microorganisms are divided into groups based on their need for oxygen. For example, aerobes (aerobic microorganisms) are microorganisms that require oxygen to grow. Another group, facultative anaerobes, are able to grow in either the presence or absence of oxygen. A third group of microorganisms are those that can grow only in the presence of very low levels of oxygen. These microorganisms are termed microaerophiles. A fourth group are microorganisms that cannot tolerate oxygen and are either inhibited or killed by it are called anaerobes (anaerobic microorganisms).

The detection of microorganisms is important in everyday life. For example, microorganisms are the cause of many diseases of man and of other mammals. In order to treat these bacterial diseases, the infecting organism must first be identified so that the correct medication and/or treatment can be prescribed. Additionally, large scale processing of food requires constant monitoring for the presence of microorganisms. Thus, the detection of microorganisms is also essential in the food processing industry.

Detecting anaerobes and microaerophiles is difficult because these microorganisms must be incubated in a controlled gaseous environment that is either oxygen free or extremely oxygen deficient. Often times an oxygen deficient environment is provided by placing a Petri dish containing the microbial culture inside a container that is sealed from the outside atmosphere. For the incubation of Petri dishes, an apparatus such as an anaerobic jar is usually employed. The container (e.g, anaerobic jar) is then depleted of oxygen by any number of means.

The anaerobic jar can mechanically be depleted of oxygen. In U.S. Pat. No. 6,022,730 to Robinson, microbial cultures were placed in an anaerobic jar that was modified to have both a gas inlet and a gas outlet. The gas line into the anaerobic jar was connected to a sterile filter in order to filter out any possible microbial contaminants in the gas reservoir or in the gas line. The anaerobic jar was sealed and periodically flushed with sterile nitrogen gas for several hours until the effluent gas contained 0% oxygen, as measured by an oximeter, to ensure an anaerobic atmosphere.

Alternatively, chemical strategies can be employed to generate an oxygen depleted or oxygen free environment. One such example of oxygen depleting chemistry is used in the BBL GasPak (Becton Dickinson, Cockeysville, Md.). Here, oxygen depletion is accomplished by the reaction of hydrogen, which is generated by the decomposition of sodium borohydride, and atmospheric oxygen in the presence of palladium to form water. Carbon dioxide is generated separately from the oxygen depletion reaction by the reaction between sodium bicarbonate and citric acid in the presence of water.

Another example of oxygen depleting chemistry is the BBL GasPak Pouch, provided by Becton Dickinson, Cockeysville, Md. The BBL GasPak Pouch is a self contained system that produces carbon dioxide and uses up atmospheric oxygen by two independent reactions. In one reaction, carbon dioxide is generated by the reaction of citric acid and inorganic carbonate. In a separate reaction, oxygen is depleted by the formation of rust from the combination of fine iron powder with atmospheric oxygen.

U.S. Pat. No. 5,914,070 to Araki, et al. describes another chemical reaction system for the depletion of oxygen. This system is based on the use of organic acids, such as ascorbic acid, which react with atmospheric oxygen in the presence of a metallic catalyst to adjust the concentration of carbon dioxide. Carbon dioxide absorbers like magnesium or calcium hydroxide are used to maintain the carbon dioxide at an overall concentration of 3–7% and the oxygen concentration to no more than 1%. This chemistry is formulated so that no activation or addition of external reagents is required. The system merely has to be exposed to oxygen to start the chemical reaction.

However, the prior art oxygen depletion methods have several drawbacks such as those listed below.

For example, in mechanical approaches such the forcible gas displacement disclosed in U.S. Pat. No. 6,022,730, it is difficult to establish uniform test conditions, especially if more than one anaerobic jar is used. Additionally, these mechanical approaches are time intensive, often requiring hours until the desired oxygen concentration is obtained. Further, there is a need for equipment maintenance since external equipment is used to pump in the gas to purge the oxygen from the anaerobic jar.

In both the BBL GasPak and the BBL GasPak Pouch, water, an external agent, must be added to initiate the oxygen depletion reaction. Thus, the GasPak reactions require extra reagents and steps for activation. Additionally, in the GasPak chemistries, the rate at which oxygen is removed is not constant. As a result, it is difficult to achieve uniform culture conditions. Further, in the BBL GasPak, a suitable catalyst such as palladium must be added to the atmosphere of the jar. Because hydrogen gas is generated, this chemistry suffers from a potential explosion hazard and therefore can be extremely dangerous.

Although the approach taken by Araki et al. in U.S. Pat. No. 5,914,070 is convenient in the fact that there is no activation required and no need to a separate reagent such as water as in the GasPak chemistries, the reaction utilized is very complicated to formulate to balance the chemistry so that the proper amount of carbon dioxide is generated. Thus, there is a need to maintain the proper concentration of carbon dioxide.

The prior art assays and devices fail to provide a simple, fast, and effective oxygen depletion method that does not require an external reagent for activation, the addition of water or other external reagents, or maintaining the level of carbon dioxide. In view of the aforementioned deficiencies attendant with the prior art methods, it is clear that a need exists for a device and method for making a suitable atmosphere for the culture of the anaerobic bacteria in a simple manner.

SUMMARY OF THE INVENTION

To achieve the foregoing and other objects, and in accordance with the purpose of the present invention as embodied and broadly described herein, the present invention provides a device that utilizes exothermic chemistry to deplete oxygen and generate carbon dioxide.

It is an object of the present invention to provide an environment suitable for the culture of anaerobic bacteria.

It is another object of the present invention to provide a device that utilizes exothermic chemistry to deplete oxygen and generate carbon dioxide to create an anaerobic environment.

It is yet another object of the present invention to provide a method for creating an anaerobic environment.

It is a further object of the present invention to provide a safe and effective method for generating an anaerobic environment suitable for the culture of anaerobic bacteria.

The above and other objects, advantages and features of the present invention will become more apparent from the following detailed description of the presently preferred embodiments, when considered in conjunction with the drawings, and to the appended claims.

DESCRIPTION OF THE PREFERRED EMBODIMENTS

Various types of exothermic heat dispensing packets known as hand warmers or hot packs are known in the art and are commercially available in sporting good stores. The activation of these packets is accomplished by various means such as exposure to air, mixing with water, kneading, or puncturing of an inner bag to mix the chemicals and start the heat generating reaction. A disposable body warmer generally contains a heat generating composition containing such chemicals as iron powder, wood flour, activated carbon, and salt.

U.S. Pat. No. 5,046,479, incorporated herein by reference, discloses an example of an air activated exothermic body warmer packet marketed by Grabber® under the trade name of Grabber Mycoal® Warm Pack. The heat generating chemistry system contains iron powder, water retaining agents such as charcoal, vermiculite, and wood flour; water, activated charcoal, and sodium chloride. The packaging consists of a flat bag that has an air-permeable surface which is capable of allowing oxygen to enter. This bag is contained in an outer wrap of an air barrier plastic film material. When the outer plastic wrapping is removed, the inner packet is exposed to air, thereby initiating the reaction of oxygen with the iron powder to form iron oxide and generate heat.

U.S. Pat. No. 3,976,049 to Yamashita, et al., also incorporated herein by reference, discloses another example of an exothermic body warmer marketed by Grabber®. This patent is directed toward the unified structure of a warmer and air tight envelope. The warmer utilizes a mixture of iron powder, water, cellulose, vermiculite, activated carbon, and salt. The iron powder is the source of heat generated by the iron contacting the salt in the presence of the water and air. The heat generating chemicals are enclosed in a laminated bag that has an air-permeable surface.

The present invention utilizes the well-known exothermic chemical reactions used in exothermic body warmers, such as the body warmers described above, together with a carbonate or bicarbonate, to generate an anaerobic environment enriched with carbon dioxide suitable for culturing anaerobic bacteria.

In particular, the present invention utilizes a heat generating composition that contains iron powder, water, activated charcoal, sodium chloride, and a water retaining agent such as charcoal, vermiculite, or wood flour in a closed environment to deplete oxygen and generate heat. The addition of a bicarbonate to the heat generating composition within the closed environment provides a source of carbon dioxide.

It is known in the art that iron powder, in the presence of water, activated charcoal, and salt, reacts with atmospheric oxygen to form iron oxide. When this reaction occurs in a closed environment, the result is the depletion of oxygen and the generation of heat. The present invention utilizes this known, heat-generating, exothermic reaction to drive the decomposition of the bicarbonate present in a closed system, which results in the release of carbon dioxide. The result of this exothermic reaction and decomposition of bicarbonate in the closed system results in a suitable oxygen depleted, carbon dioxide enriched atmospheric environment which is particularly suitable for the growth of anaerobic bacteria.

With respect to the heat generating composition of the present invention, a heat generating chemistry such as is disclosed in U.S. Pat. No. 5,046,479 is suitable for use in the present invention. As is described in U.S. Pat. No. 5,046,479, a suitable heat generating composition can comprise iron powder as the main ingredient with water retained in a water retaining material such as charcoal or vermiculite, and an oxidation promoter such as activated carbon and salt. In particular, the heat generating composition contains about 55–65% by weight iron powder, about 9–11% by weight of a water retaining agent, about 18–22% by weight water, about 3–5% by weight activated carbon, and about 4–6% by weight salt. However, any of the heat warming chemistries that utilize iron powder to deplete oxygen and generate heat can be used as the heat generating composition of the present invention.

The addition of a bicarbonate to the heat generating composition described above provides a reactant to the heat generated by the heat generating composition to generate carbon dioxide. Preferably, the bicarbonate is included in the heat generating composition. However, the bicarbonate can be added as a separate component provided that adequate heat transfer from the exothermic composition can be obtained for the bicarbonate to effect the release of carbon dioxide. When the above combination is placed inside a closed, air-tight container, and the heat generating composition is exposed to oxygen, the result is a rapid depletion of oxygen within the container and the generation of carbon dioxide gas. The amount of carbon dioxide generated in the container depends on the amount of bicarbonate included within the composition.

Any alkali bicarbonate is suitable for use in the present invention, although sodium bicarbonate is most preferred. Suitable examples include sodium bicarbonate, potassium bicarbonate, magnesium bicarbonate, calcium bicarbonate, and hydrates thereof. The specific amount of bicarbonate to be added to the composition is dependent upon the size of the container and the amount of carbon dioxide to be generated. Care needs to be taken to ensure that excessive pressures are not generated within the sealed container by the in situ generation of carbon dioxide gas. In a preferred embodiment, a pressure relief mechanism may be employed to release the pressure within the container.

A device and method for accomplishing the above process will now be described. The heat generating composition and, preferably, the bicarbonate can be placed within a package consisting of a flat bag having an air-permeable surface capable of permitting oxygen to enter the bag and be consumed by the iron powder to form iron oxide and generate heat. Preferably, the bag is contained within an outer wrap consisting of a plastic film material forming an air barrier to the bag. To activate the heat generating composition, the outer wrap is removed to expose the inner bag to the oxygen within the container.

Alternatively, the bicarbonate can be placed within the package adjacent to the heat generating composition within the inner bag. The supply of bicarbonate must be positioned so as to obtain a sufficient heat transfer from the separate heat generating composition when exposed to the air due to the removal of the outer wrap to decompose the bicarbonate. In this alternative embodiment, the heat generating composition and the bicarbonate can be placed in separate packages provided that the packages are placed in close contact to obtain adequate heat transfer therebetween.

In operation, the above-described device will generate an anaerobic environment. The device of the present invention is placed in a sealed container and the outer wrap is removed from the package to expose air permeable bag. The heat generating composition within the air-permeable bag reacts with the oxygen within the container to form iron oxide and generate heat. The heat generated from this oxidative generation reaction causes the bicarbonate present in the package to decompose and generate carbon dioxide. The desired amount of carbon dioxide gas can be controlled by limiting the amount of bicarbonate in the package to be decomposed by the generated heat. The end result is an oxygen depleted, carbon dioxide enriched atmospheric environment suitable for the growth of anaerobic bacteria.

In certain situations, heat alone is not enough to provide sufficient carbon dioxide within the container. Alternatively, a dry acid such as citric acid or ascorbic acid, together with a bicarbonate in the presence of water, can be used to aid in the generation of carbon dioxide.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. Numerous variations may be made by persons skilled in the art without departure from the spirit of the invention. The scope of the invention will be measured by the appended claims and their equivalents.

EXAMPLES

Example 1

Generation of Anaerobic Environment

Materials

GasPak™ Plus® environmental system for anaerobes

"Warm Pack" air-activated warmers (Grabber Mycoal®)

Test organisms (see Table 1)

Quality control organisms (see Table 2)

Media (CDC ANA, TSA II)

2.5 L GasPak incubation jars

TABLE 1

Organisms used in evaluation.

| Organism | Media |
|---|---|
| Fusobacterium sp. | CDC ANA |
| Bacteroides sp. | CDC ANA |
| Clostridium sp. | CND ANA |
| Proprionibacterium sp. | CDC ANA |
| Peptostreptococcus sp. | CDC ANA |
| Veillonella sp. | CDC ANA |
| Micrococcus sp. | CDC ANA + TSA II |
| Acinetobacter sp. | CDC ANA + TSA II |

TABLE 2

Quality control organisms used in evaluation.

| Organism | Strain | Media |
|---|---|---|
| Bacteroides fragilis | ATCC ® 25285 | CDC ANA |
| Clostridium perfringens | ATCC ® 13124 | CDC ANA |
| Peptostreptococcus anaerobius | ATCC ® 27337 | CDC ANA |

Method

Clinical Isolates

Isolated colonies (organisms from Table 1) were picked from a fresh culture that was 24–48 hours old. A 0.5 McFarland suspension in sterile saline was prepared and then diluted 1:10. Duplicate plates with 0.1 ml of the 1:10 suspension were inoculated. The plates were streaked for isolation as described in "Plate Inoculation" set forth below.

Plate Inoculation

Each plate was streaked for isolation using the procedure described below:

Quadrant 1: Place inoculum using a sterile pipette. Spread using a sterile plastic loop.

Quadrant 2: Streak back into Quadrant 1 eight times, turn loop over.

Quadrant 3: Steak back into Quadrant 2 four times.

Quadrant 4: Using the same side of the loop as for Quadrant 3, streak back into Quadrant 3 two times for isolation of colonies in Quadrant 4.

Incubation of Plates

Plates were incubated at 35° C.±2° for 24–48 hours. One set of plates was incubated in a 2.5 L capacity GasPak 100 ® jar with a GasPak Plus gas generating envelope, and one set of plates was incubated in a 2.5 L GasPak anaerobic jar with a "Warm Pack" sachet.

Plate Quantification

After incubation, each set of plated media was read.

Semi-quantitative colony size and colony counts were recorded for each set of plates using the criteria set forth below in "Final Results Assignment". The results are set forth in Tables 3–5.

Final Results Assignment

Any system from which bacteria was recovered was quantitated by the following criteria:

Growth Scores

0   No growth on plate.
1   10 or fewer colonies in Quadrant 1; no growth in higher quadrant.
2   >10 colonies in Quadrant 1; no more than one colony in Quadrant 2; no growth in higher quadrants.
3   2 to 10 colonies in Quadrant 2; no growth in higher quadrants.
4   >10 colonies in Quadrant 2; no more than 1 colony in Quadrant 3; no growth in Quadrant 4.
5   2 to 10 colonies in Quadrant 3; no growth in Quadrant 4.
6   >10 colonies in Quadrant 3; no more than 1 colony in Quadrant 4.
7   2 to 10 colonies in Quadrant 4.
8   >10 colonies in Quadrant 4.

Colony Size (if applicable)

Pinpoint = <1 mm
Small = 1–2 mm
Medium = 3–4 mm
Large = >5 mm

Quality Control

Quality control isolates (organisms from Table 2) accompanied each batch of inoculated media in the routine and test environment.

a. A 0.5 McFarland suspension in sterile was prepared. The suspension was inoculated 1:10 to create the inoculum suspension. Duplicate plates with 0.1 ml of the suspension were inoculated. Each plate was streaked using the procedure described above in "Plate Inoculation".

b. Plates were incubated at 35° C.±2° for 24–48 hours. One set of plates was incubated in a 2.5 L capacity GasPak 100® jar with a GasPak Plus gas generating envelope, and one set of plates was incubated in a 2.5 L GasPak anaerobic jar with a "Warm Pack" or Hot Hands® sachet or their contents.

c. Expected Results:
   *Bacteroides fragilis* typically yields $5.0 \times 10^8$ CFU/ml and a growth score of 4.
   *Clostridium perfringens* typically yields $5.0 \times 10^6$ CFU/ml and a growth score of 6.
   *Peptostreptococcus anaerobius* typically yields $1.0 \times 10^6$ CFU/ml and a growth score of 6.

d. Quality Control data was recorded.

Results

TABLE 3

| Date | Isolate | GasPak Plus Growth Score | GasPak Plus Colony Size | "Warm Pack" Growth Score | "Warm Pack" Colony Size |
|---|---|---|---|---|---|
| Jul. 24, 2000 | *M. luteus* 9341 | 8 | Small | 8 | Pinpoint |
| | *V. parvula* 10790 | 8 | | 8 | |
| | *F. necrophorum* 25286 | 8 | | 5 | |
| | *P. magnus* 14956 | 8 | | 8 | |
| | *P. acnes* 11827 | 8 | | 8 | |
| | *C. sordelli* 9714 | 8 | | 7 | |
| | *Acinetobacter sp.* 33604 | 8 | Medium | 8 | Small |

Growth Scores
0 No growth on plate.
1 10 or fewer colonies in Quadrant 1; no growth in higher quadrant.
2 >10 colonies in Quadrant 1; no more than one colony in Quadrant 2; no growth in higher quadrants.
3 2 to 10 colonies in Quadrant 2; no growth in higher quadrants.
4 >10 colonies in Quadrant 2; no more than 1 colony in Quadrant 3; no growth in Quadrant 4.

TABLE 3-continued 5 2 to 10 colonies in Quadrant 3; no growth in Quadrant 4.
6 >10 colonies in Quadrant 3; no more than 1 colony in Quadrant 4.
7 2 to 10 colonies in Quadrant 4.
8 >10 colonies in Quadrant 4.
Colony Size (if applicable)
Pinpoint = <1 mm
Small = 1–2 mm
Medium = 3–4 mm
Large = >5 mm

TABLE 4

"Warm Pack" Sachets

| Isolate | Growth Score | Colony Size |
|---|---|---|
| *B. vulgatus* 29327 | 7 | |
| *P. magnus* 14956 | 8 | |
| *B. ovatus* 700292 | 8 | Pinpoint |
| *P. intermedica* 25261 | 0 | |
| *F. nucleatum* 10953 | 0 | |
| *F. nucleatum* 25586 | 0 | |
| *B. ovatus* 8482 | 6 | |
| *P. intermedica* 25611 | 0 | |
| *F. mortiferum* 9817 | 8 | |
| *F. mortiferum* 25557 | 8 | |
| *V. parvula* 10790 | 8 | |
| *C. perfringens* 10543 | 7 | |
| *F. necrophorum* 25286 | 0 | |
| *C. sordelli* 9714 | 5 | |
| *V. parvula* 35184 | 8 | |
| *P. magnus* 29328 | 3 | |
| *P. acnes* 11827 | 7 | |
| *F. lentum* 25559 | 0 | |
| *C. sordelli* 14337 | 7 | |
| *E. lentum* 43055 | 0 | |
| *B. theta.* 12290 | 6 | Pinpoint |
| *B. theta.* 29741 | 8 | Pinpoint |
| *C. perfringens* 3624 | 8 | |

TABLE 5

Effects of "Warm Packs" Plus $CO_2$ on Recovery of Anaerobes

| Organism | GasPak Plus Growth Score | GasPak Plus Colony Size | Warm Pack (1) Growth Score | Warm Pack (1) Colony Size | Warm Pack (2) Growth Score | Warm Pack (2) Colony Size | Warm Pack (1)/$CO_2$ Growth Score | Warm Pack (1)/$CO_2$ Colony Size | Warm Pack (2)/$CO_2$ Growth Score | Warm Pack (2)/$CO_2$ Colony Size |
|---|---|---|---|---|---|---|---|---|---|---|
| *P. intermedica* 25261 | 8 | | 7 | | 6 | | 6 | | 7 | |
| *F. nucleatum* 10953 | 6 | | 0 | | 0 | | 5 | | 0 | |
| *B. fragilis* 25285 | 8 | Medium | 0 | | 0 | | 5 | Pinpoint | 7 | Small |

TABLE 5-continued

Effects of "Warm Packs" Plus $CO_2$ on Recovery of Anaerobes

| Organism | GasPak Plus | | Warm Pack (1) | | Warm Pack (2) | | Warm Pack (1)/$CO_2$ | | Warm Pack (2)/$CO_2$ | |
|---|---|---|---|---|---|---|---|---|---|---|
| | Growth Score | Colony Size | Growth Score | Colony Size | Growth Score | Colony Size | Growth Score | Colony Size | Growth Score | Colony Size |
| E. lentum 25559 | 6 | | 0 | | 0 | | 6 | | 0 | |
| E. lentum 43055 | 6 | | 0 | | 0 | | 6 | | 1 | |
| F. nucleatum 25586 | 8 | | 0 | | 0 | | 1 | | 0 | |

Example 2

Environment Conditioning:

Hot Hands® sachet is a "Self Activating Hand and Body Warmer" made by Heatmax Corp., USA, with iron-based oxygen reactants. The contents from each sachet were mixed respectively with 5, 10, or 15 grams of sodium bicarbonate (baking soda).

Growth Medium:

The growth medium was CDC Anaerobic Blood Agar (BBL 4321734).

Incubation of Plates:

Plates were incubated at 35° C. for a approximately 48 hours.

Plate Quantification:

After 48 hours of incubation at 35° C., each set of plated media was read.

Semi-quantitative colony counts were recorded for each set of plates using the criteria set forth below in "Final Results Assignment".

Final Results Assignment:

Any system from which bacteria was recovered was quantitated by the following criteria:

Growth score reading (average of three sachets per score):

0=No growth on plate.
1=10 colonies in Quadrant 1.
2=10 colonies in Quadrant 1.
4=10 colonies in Quadrant 2.
6=10 colonies in Quadrant 3.
7=>10 colonies in Quadrant 4.

Results:

The results are set forth in Table 6.

TABLE 6

Select $CO_2$ Sensitive Fastidious Anaerobic Organism *Hot Hands ® $NaHCO_3$ Mix[a,b]

| Fastidious Anaerobic Organism | ATCC | Bicarbonate Admix | | | |
|---|---|---|---|---|---|
| | | 0 g | 5 g | 10 g | 15 g |
| Fusobacterium nucleateum | 10953 | 0[3] | 0 | 1.67 | 4.33 |
| Eubacterium lentum | 25659 | 0 | 0 | 6.67 | 6.67 |
| Bacteroides fragilis | 25285 | 0 | 7.33 | 7.67 | 7.67 |
| Eubacterium lentum | 43055 | 0 | 0 | 2.67 | 6.67 |

[a]$CO_2$ is released from sodium bicarbonate at a temperature exceeding 50° C.
[b]Temperatures greater than 50° C. are generated by Hot Hands ® reactants within 5 to 10 minutes and can rise to greater than 90° C. beyond 10 minutes when exposed to air.

What is claimed is:

1. A composition for creating an anaerobic environment in a container comprising a heat generating, oxygen depleting composition comprising iron powder, a water retaining agent, water, activated charcoal, and sodium chloride and a carbon dioxide generating material.

2. The composition of claim 1, wherein said carbon dioxide generating material includes citric acid.

3. The composition of claim 1, wherein said carbon dioxide generating material includes ascorbic acid.

4. The composition of claim 1, wherein said carbon dioxide generating material is a bicarbonate.

5. The composition of claim 4, wherein said bicarbonate is selected from the group consisting of sodium bicarbonate, calcium bicarbonate, potassium bicarbonate and magnesium bicarbonate.

* * * * *